(12) United States Patent
Bhatnagar et al.

(10) Patent No.: US 10,953,214 B2
(45) Date of Patent: Mar. 23, 2021

(54) HEMOSTASIS VALVES AND METHODS FOR MAKING AND USING HEMOSTASIS VALVES

(71) Applicant: BOSTON SCIENTIFIC LIMITED, Hamilton (BM)

(72) Inventors: Mayank Bhatnagar, Delhi (IN); Sohail Rahmani, Galway (IE); Alan James O'Flynn, Co. Tipperary (IE); Poornachandra Nayak, Karnataka (IN); Peeyush Tomar, Muzaffarnagar (IN); Somashekar Reddy, Mysore (IN); Seamus McGurran, Galway (IE); John McSweeney, Cork (IE); Henry J. Pepin, Loretto, MN (US); Deepak Bhardwaj, Firozpur (IN); Nilesh Raghunath Barhate, Pune (IN)

(73) Assignee: BOSTON SCIENTIFIC LIMITED, Hamilton (BM)

( * ) Notice: Subject to any disclaimer, the term of this patent is extended or adjusted under 35 U.S.C. 154(b) by 269 days.

(21) Appl. No.: 16/128,068

(22) Filed: Sep. 11, 2018

(65) Prior Publication Data

US 2019/0076640 A1 Mar. 14, 2019

Related U.S. Application Data

(60) Provisional application No. 62/557,706, filed on Sep. 12, 2017.

(51) Int. Cl.
*A61M 39/06* (2006.01)
(52) U.S. Cl.
CPC .... *A61M 39/0613* (2013.01); *A61M 39/0693* (2013.01); *A61M 2039/0626* (2013.01);
(Continued)

(58) Field of Classification Search
CPC .......... A61M 39/0613; A61M 39/0693; A61M 2039/0626; A61M 2039/0673;
(Continued)

(56) References Cited

U.S. PATENT DOCUMENTS 2,023,267 A 12/1935 De Saint Rapt et al.
2,833,568 A 5/1958 Corsette
(Continued)

FOREIGN PATENT DOCUMENTS

DE 29701600 U1 7/1997
EP 0567142 A2 10/1993
(Continued)

OTHER PUBLICATIONS

PCT Search Report and Written Opinion for PCT/US2009/039396 dated Apr. 3, 2009.
(Continued)

*Primary Examiner* — Theodore J Stigell
*Assistant Examiner* — Daniel Moore
(74) *Attorney, Agent, or Firm* — Seager, Tufte & Wickhem LLP.

(57) ABSTRACT

Hemostasis valves and methods for making and using hemostasis valves are disclosed. An example hemostasis valve may include a main body having a distal end region and a proximal end region. A first seal member may be disposed within the proximal end region of the main body. A plunger may be coupled to the proximal end region of the main body. The plunger may be designed to shift between a first position and a second position. A first locking member may be disposed along the proximal end region of the main body. A second locking member may be disposed along the plunger. The second locking member may be designed to engage the first locking member.

18 Claims, 15 Drawing Sheets

(52) U.S. Cl.
CPC .......... *A61M 2039/0633* (2013.01); *A61M 2039/0673* (2013.01); *A61M 2039/0686* (2013.01)

(58) Field of Classification Search
CPC .. A61M 2039/0633; A61M 2039/0686; A61M 39/06; A61M 2039/062
See application file for complete search history.

(56) References Cited

U.S. PATENT DOCUMENTS

| | | |
|---|---|---|
| 3,095,175 A | 6/1963 | Taisho |
| 3,180,334 A | 4/1965 | Glenn |
| 3,685,786 A | 8/1972 | Woodson |
| 4,000,739 A | 1/1977 | Stevens |
| 4,177,814 A | 12/1979 | Knepshield et al. |
| 4,240,411 A | 12/1980 | Hosono |
| 4,424,833 A | 1/1984 | Spector et al. |
| 4,430,081 A | 2/1984 | Timmermans |
| 4,436,519 A | 3/1984 | O'Neill |
| 4,610,655 A | 9/1986 | Mueller |
| 4,612,010 A | 9/1986 | Hamacher et al. |
| 4,615,531 A | 10/1986 | Green |
| 4,626,245 A | 12/1986 | Weinstein |
| 4,629,450 A | 12/1986 | Suzuki et al. |
| 4,655,752 A | 4/1987 | Honkanen et al. |
| 4,673,393 A | 6/1987 | Suzuki et al. |
| 4,705,511 A | 11/1987 | Kocak |
| 4,723,550 A | 2/1988 | Bales et al. |
| 4,726,374 A | 2/1988 | Bales et al. |
| 4,798,594 A | 1/1989 | Hillstead |
| 4,857,062 A | 8/1989 | Russell |
| 4,875,062 A | 10/1989 | Rakov |
| 4,895,346 A | 1/1990 | Steigerwald |
| 4,895,565 A | 1/1990 | Hillstead |
| 4,909,798 A | 3/1990 | Fleischhaker et al. |
| 4,917,668 A | 4/1990 | Haindl |
| 4,925,450 A | 5/1990 | Imonti et al. |
| 4,932,114 A | 6/1990 | Morse et al. |
| 4,932,633 A | 6/1990 | Johnson et al. |
| 4,960,412 A | 10/1990 | Fink |
| 4,978,341 A | 12/1990 | Niederhauser |
| 5,000,745 A | 3/1991 | Guest et al. |
| 5,009,391 A | 4/1991 | Steigerwald |
| 5,030,206 A | 7/1991 | Lander |
| 5,041,095 A | 8/1991 | Littrell |
| 5,049,071 A | 9/1991 | Davis et al. |
| 5,059,186 A | 10/1991 | Yamamoto et al. |
| 5,060,987 A | 10/1991 | Miller |
| 5,078,433 A | 1/1992 | Morse et al. |
| 5,078,688 A | 1/1992 | Lobodzinksi et al. |
| 5,098,393 A | 3/1992 | Amplatz et al. |
| 5,106,054 A | 4/1992 | Mollenauer et al. |
| 5,114,408 A | 5/1992 | Fleischhaker et al. |
| 5,125,903 A | 6/1992 | McLaughlin et al. |
| 5,135,492 A | 8/1992 | Melker et al. |
| 5,149,327 A | 9/1992 | Oshiyama |
| 5,154,701 A | 10/1992 | Cheer et al. |
| 5,158,553 A | 10/1992 | Berry et al. |
| 5,161,773 A | 11/1992 | Tower |
| 5,167,636 A | 12/1992 | Clement |
| 5,167,637 A | 12/1992 | Okada et al. |
| 5,176,652 A | 1/1993 | Littrell |
| 5,195,980 A | 3/1993 | Catlin |
| 5,197,463 A | 3/1993 | Jeshuran |
| 5,203,774 A | 4/1993 | Gilson et al. |
| 5,205,831 A | 4/1993 | Ryan et al. |
| 5,207,656 A | 5/1993 | Kranys |
| 5,224,929 A | 7/1993 | Remiszewski |
| 5,241,990 A | 9/1993 | Cook |
| 5,269,764 A | 12/1993 | Vetter et al. |
| 5,269,771 A | 12/1993 | Thomas et al. |
| 5,273,546 A | 12/1993 | McLaughlin et al. |
| 5,282,790 A | 2/1994 | Clement |
| 5,299,843 A | 4/1994 | Weigl et al. |
| 5,324,271 A | 6/1994 | Abiuso et al. |
| 5,338,313 A | 8/1994 | Mollenauer et al. |
| 5,350,205 A | 9/1994 | Aldridge et al. |
| 5,350,364 A | 9/1994 | Stephens et al. |
| 5,352,215 A | 10/1994 | Thome et al. |
| 5,356,394 A | 10/1994 | Farley et al. |
| 5,364,371 A | 11/1994 | Kamen |
| 5,376,077 A | 12/1994 | Gomringer |
| 5,382,230 A | 1/1995 | Bonn |
| 5,383,860 A | 1/1995 | Lau |
| 5,389,090 A | 2/1995 | Fischell et al. |
| 5,395,349 A | 3/1995 | Quiachon et al. |
| 5,460,615 A | 10/1995 | Storz |
| 5,514,109 A | 5/1996 | Mollenauer et al. |
| 5,520,655 A | 5/1996 | Davila et al. |
| 5,542,933 A | 8/1996 | Marks |
| 5,562,611 A | 10/1996 | Transue |
| 5,569,208 A | 10/1996 | Woelpper et al. |
| 5,575,767 A | 11/1996 | Stevens |
| 5,584,314 A | 12/1996 | Bron |
| 5,591,137 A | 1/1997 | Stevens |
| 5,599,327 A | 2/1997 | Sugahara et al. |
| 5,643,227 A | 7/1997 | Stevens |
| 5,651,170 A | 7/1997 | Stevens |
| 5,693,025 A | 12/1997 | Stevens |
| 5,779,697 A | 7/1998 | Glowa et al. |
| 5,858,007 A | 1/1999 | Fagan et al. |
| 5,911,710 A | 6/1999 | Barry et al. |
| 5,921,968 A | 7/1999 | Lampropoulos et al. |
| 5,935,112 A | 8/1999 | Stevens et al. |
| 5,935,122 A | 8/1999 | Fourkas et al. |
| 5,992,899 A | 11/1999 | Strowe |
| 6,024,729 A | 2/2000 | Dehdashtian et al. |
| 6,149,632 A | 11/2000 | Landuyt |
| 6,277,100 B1 | 8/2001 | Raulerson et al. |
| 6,287,280 B1 | 9/2001 | Lampropoulos et al. |
| 6,331,176 B1 | 12/2001 | Becker et al. |
| 6,402,723 B1 | 6/2002 | Lampropoulos et al. |
| 6,458,103 B1 | 10/2002 | Albert et al. |
| 6,551,283 B1 | 4/2003 | Guo et al. |
| 6,572,590 B1 | 6/2003 | Stevens et al. |
| 6,632,200 B2 | 10/2003 | Guo et al. |
| 6,695,818 B2 | 2/2004 | Wollschlger |
| 6,986,749 B2 | 1/2006 | Wollschlger |
| 7,081,106 B1 | 7/2006 | Guo et al. |
| 7,172,580 B2 | 2/2007 | Hruska et al. |
| 7,938,809 B2 | 5/2011 | Lampropoulos et al. |
| 8,777,893 B2 | 7/2014 | Malewicz |
| 9,592,372 B2 | 3/2017 | Myers |
| 2001/0021825 A1 | 9/2001 | Becker et al. |
| 2002/0010425 A1 | 1/2002 | Guo et al. |
| 2004/0172008 A1 | 9/2004 | Layer |
| 2004/0210194 A1* | 10/2004 | Bonnette .......... A61B 17/32037 604/167.06 |
| 2005/0033239 A1 | 2/2005 | Argentine |
| 2005/0171479 A1 | 8/2005 | Hruska et al. |
| 2007/0106262 A1 | 5/2007 | Becker et al. |
| 2008/0157017 A1 | 7/2008 | Macatangay et al. |
| 2008/0208175 A1 | 8/2008 | Beckman et al. |
| 2009/0259200 A1 | 10/2009 | Lampropoulos et al. |
| 2013/0006176 A1 | 1/2013 | Miller |
| 2014/0207083 A1* | 7/2014 | Pessin .................. A61M 39/06 604/256 |
| 2018/0126143 A1 | 5/2018 | Agrawal et al. |

FOREIGN PATENT DOCUMENTS

| | | | |
|---|---|---|---|
| WO | 9813083 | A1 | 4/1998 |
| WO | 9945983 | A1 | 9/1999 |
| WO | 0062844 | A1 | 10/2000 |
| WO | 0117587 | A1 | 3/2001 |
| WO | 2005018732 | A1 | 3/2005 |
| WO | 2009139981 | A2 | 11/2009 |

OTHER PUBLICATIONS

International Search Report and Written Opinion dated Jun. 20, 2018 for International Application No. PCT/US2018/019712.

(56) References Cited

OTHER PUBLICATIONS

International Search Report and Written Opinion for Application No. PCT/US20181020202, 14 pages, dated May 25, 2018.
International Search Report and Written Opinion for Application No. PCT/US2018/020214, 17 pages, dated May 15, 2018.
International Search Report and Written Opinion for Application No. PCT/US20181019674, 13 pages, dated Jun. 13, 2018.
International Search Report and Written Opinion for Application No. PCT/US2018/019479, 13 pages, dated May 22, 20111.
International Search Report and Written Opinion for Application No. PCT/US2018/050456, 24 pages, dated Nov. 6, 2018.

* cited by examiner

HEMOSTASIS VALVES AND METHODS FOR MAKING AND USING HEMOSTASIS VALVES

CROSS-REFERENCE TO RELATED APPLICATIONS

This application claims priority under 35 U.S.C. § 119 to U.S. Provisional Application Ser. No. 62/557,706, filed Sep. 12, 2017, the entirety of which is incorporated herein by reference.

TECHNICAL FIELD

The present disclosure pertains to medical devices, and methods for manufacturing medical devices. More particularly, the present disclosure pertains to hemostasis valves and methods for making and using hemostasis valves.

BACKGROUND

A wide variety of medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device includes a hemostasis valve. The hemostasis valve comprises: a main body having a distal end region and a proximal end region; a first seal member disposed within the proximal end region of the main body; a plunger coupled to the proximal end region of the main body, the plunger being designed to shift between a first position and a second position; a first locking member disposed along the proximal end region of the main body; and a second locking member disposed along the plunger, the second locking member being designed to engage the first locking member.

Alternatively or additionally to any of the embodiments above, further comprising a cartridge at least partially disposed within the proximal end region of the main body, wherein the first seal is within the cartridge.

Alternatively or additionally to any of the embodiments above, the first seal member is designed to be in a natively closed configuration.

Alternatively or additionally to any of the embodiments above, the plunger is designed to open the first seal member when shifted to the second position.

Alternatively or additionally to any of the embodiments above, the plunger is designed to engage the first locking member with the second locking member and maintain the plunger in the second position.

Alternatively or additionally to any of the embodiments above, the first locking member includes a first projection region disposed along the proximal end region of the main body and extending radially outward from the proximal end region of the main body.

Alternatively or additionally to any of the embodiments above, the first locking member includes an annular region having an opening formed therein.

Alternatively or additionally to any of the embodiments above, a shoulder region is defined adjacent to the first projection region.

Alternatively or additionally to any of the embodiments above, the second locking member includes a second projection region disposed along the plunger extending radially inward from the plunger.

Alternatively or additionally to any of the embodiments above, further comprising: a rib disposed along the proximal end region of the main body; a slot disposed along the plunger, the slot configured to receive the rib; and an alignment member disposed along an outer surface of the plunger, the alignment member corresponding to a position of the slot.

Alternatively or additionally to any of the embodiments above, further comprising: a second seal member disposed at least partially within the main body; and a compression member coupled to the proximal end region of the main body, the compression member being designed to shift the second seal member between an open configuration and a sealed configuration.

Alternatively or additionally to any of the embodiments above, the plunger is designed to rotate the compression member and shift the second seal member to the sealed configuration when the plunger is rotated in a first direction while the plunger is at the second position, and wherein the plunger is designed to engage the first locking member with the second locking member and maintain the plunger in the second position when the plunger is rotated in a second direction different from the first direction while the plunger is at the second position.

Alternatively or additionally to any of the embodiments above, the compression member includes a nut threadably engaged with an external thread disposed along an outer surface of the proximal end region of the main body.

Alternatively or additionally to any of the embodiments above, the compression member includes a nut threadably engaged with an internal thread disposed along an inner surface of the proximal end region of the main body.

A hemostasis valve is disclosed. The hemostasis valve comprises: a main body having a distal end region and a proximal end region; a cartridge at least partially disposed within the proximal end region of the main body, the cartridge including a first seal member; wherein the first seal member is designed to be in a natively closed configuration; a second seal member disposed within the proximal end region of the main body; a nut coupled to the proximal end region of the main body, the nut being designed to shift the second seal member between an open configuration and a sealed configuration; a plunger coupled to the proximal end region of the main body, the plunger being designed to shift between a first axial position and a second axial position; wherein shifting the plunger to the second axial position opens the first seal member; a first locking member disposed along the proximal end region of the main body; a second locking member disposed along the plunger; wherein rotating the plunger in a first direction while the plunger is at the second axial position rotates the nut and shifts the second seal member from the open configuration to the sealed configuration; and wherein rotating the plunger in a second direction while the plunger is at the second axial position engages the first locking member with the second locking member and maintains the plunger at the second axial position.

Alternatively or additionally to any of the embodiments above, the nut is threadably engaged with an external thread disposed along an outer surface of the proximal end region of the main body.

Alternatively or additionally to any of the embodiments above, the nut is threadably engaged with an internal thread disposed along an inner surface of the proximal end region of the main body.

Alternatively or additionally to any of the embodiments above, the first locking member includes a first projection disposed along the proximal end region of the main body and extending radially outward from the proximal end region of the main body, wherein a shoulder region is defined along the first projection.

A method for using a hemostasis valve is disclosed. The method comprises: securing a hemostasis valve to a medical device, the hemostasis valve comprising: a main body having a distal end region and a proximal end region; a seal member disposed within the proximal end region of the main body, wherein the seal member is designed to be in a natively closed configuration, and a plunger coupled to the proximal end region of the main body, the plunger being designed to shift between a first axial position and a second axial position, a first locking member disposed along the proximal end region of the main body, and a second locking member disposed along the plunger; shifting the plunger to the second axial position to open the seal member; and rotating the plunger in a first direction while the plunger is at the second axial position to engage the first locking member with the second locking member and maintain the plunger at the second axial position.

Alternatively or additionally to any of the embodiments above, further comprising rotating the plunger in a second direction opposite the first direction while the plunger is at the second axial position.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
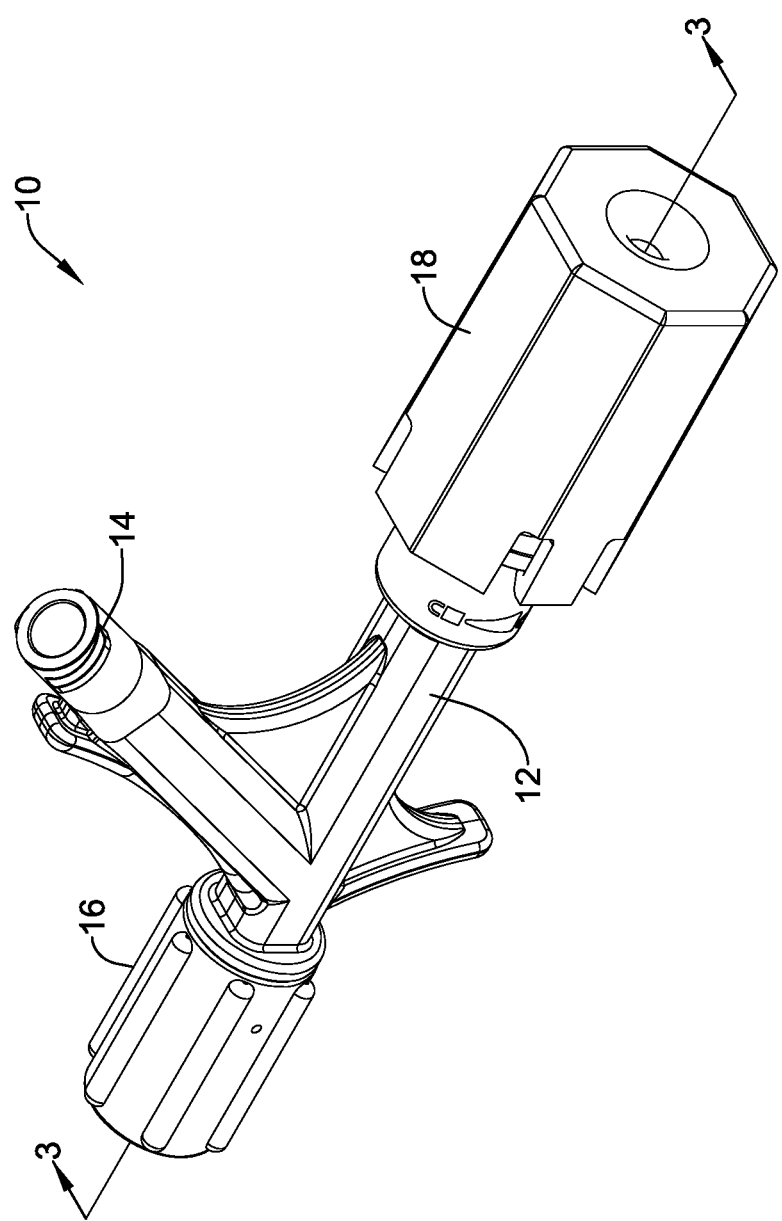
FIG. 1 is a perspective view of an example hemostasis valve.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

A number of medical procedures, for example intravascular procedures, utilize medical devices within body lumens. For example, some intravascular procedures include the placement of a guidewire, guide catheter, interventional device, or the like in a blood vessel. Because fluid under pressure (e.g., blood) is present within the blood vessel, fluid could travel along or through the medical device and escape or leak from the patient. In some instances, it may be desirable to dispose a hemostasis valve or hemostasis valve assembly at the proximal end of a medical device to reduce or otherwise limit the leaking of fluids/blood from the proximal end of the device.

An example hemostasis valve 10 is shown in FIG. 1. The hemostasis valve 10 may include a main body 12. The main body 12 may include a side port 14. The side port 14 may be connected to another device such as an infusion device, an inflation device, or the like. An adapter 16 may be coupled to the distal end of the main body 12. The adapter 16 may be used to couple the hemostasis valve 10 to a device such as a catheter. A plunger 18 may be coupled to the proximal end of the main body 12. The plunger 18 may be used to activate or otherwise close a seal (e.g., as discussed herein) within the hemostasis valve 10. These and other features of the hemostasis valve 10 are discussed herein.

Figure 2:
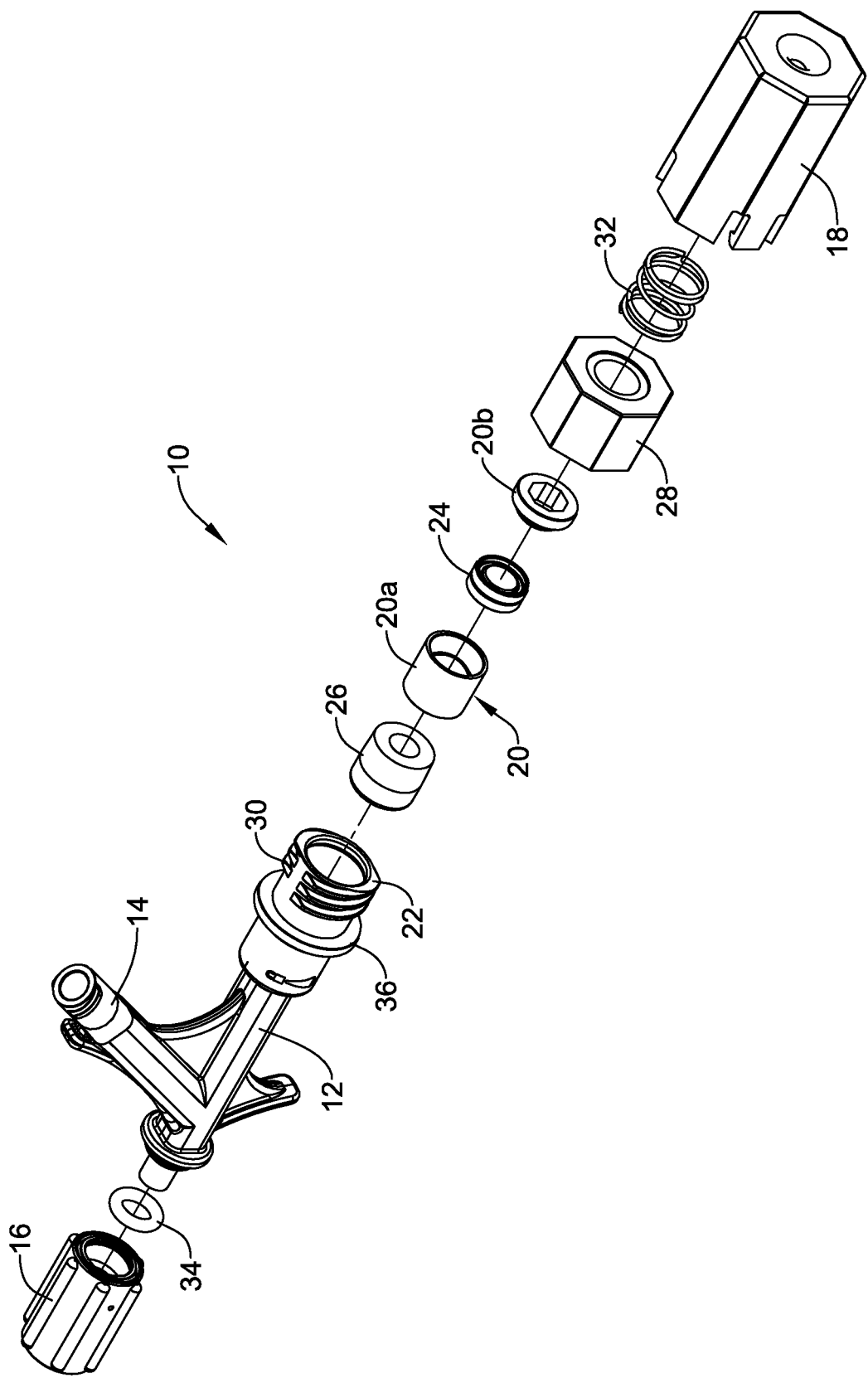
FIG. 2 is an exploded view of an example hemostasis valve.

FIG. 2 is an exploded view of the hemostasis valve 10. Here, the various components of the hemostasis valve 10 can be seen. For example, the hemostasis valve 10 may include a cartridge 20. The cartridge 20, which may include two pieces 20a, 20b that are coupled to one another (e.g., press fit, thermally bonded, adhesively bonded, etc.), may be arranged so that at least a portion thereof can be disposed within a proximal end region 22 of the main body 12. A first seal member 24 may be disposed within the cartridge 20. A second seal member 26 may be disposed within the proximal end region 22 of the main body 12. In at least some instances, the second seal member 26 may be disposed distally of the cartridge 20. The second seal member 26 may include a textured distal surface, grooves or wells formed therein, or the like. In addition or in the alternative, the second seal member 26 may include a proximal region with a reduced diameter. A nut 28 may be coupled to the proximal end region 22 of the main body 12, for example at one or more threads 30 formed along the proximal end region 22.

Other features of the hemostasis valve 10 that can be seen in FIG. 2 include a spring member 32 and an O-ring 34. The spring member 32 may be coupled to the plunger 18. In at least some instances, the spring member 32 may be designed to exert a proximally directed force on the plunger 18. The O-ring 34 may be positioned adjacent to the adapter 16. In addition, a ring member or "snap ring" 36 may be disposed along the proximal end region 22 of the main body 12.

Figure 3:
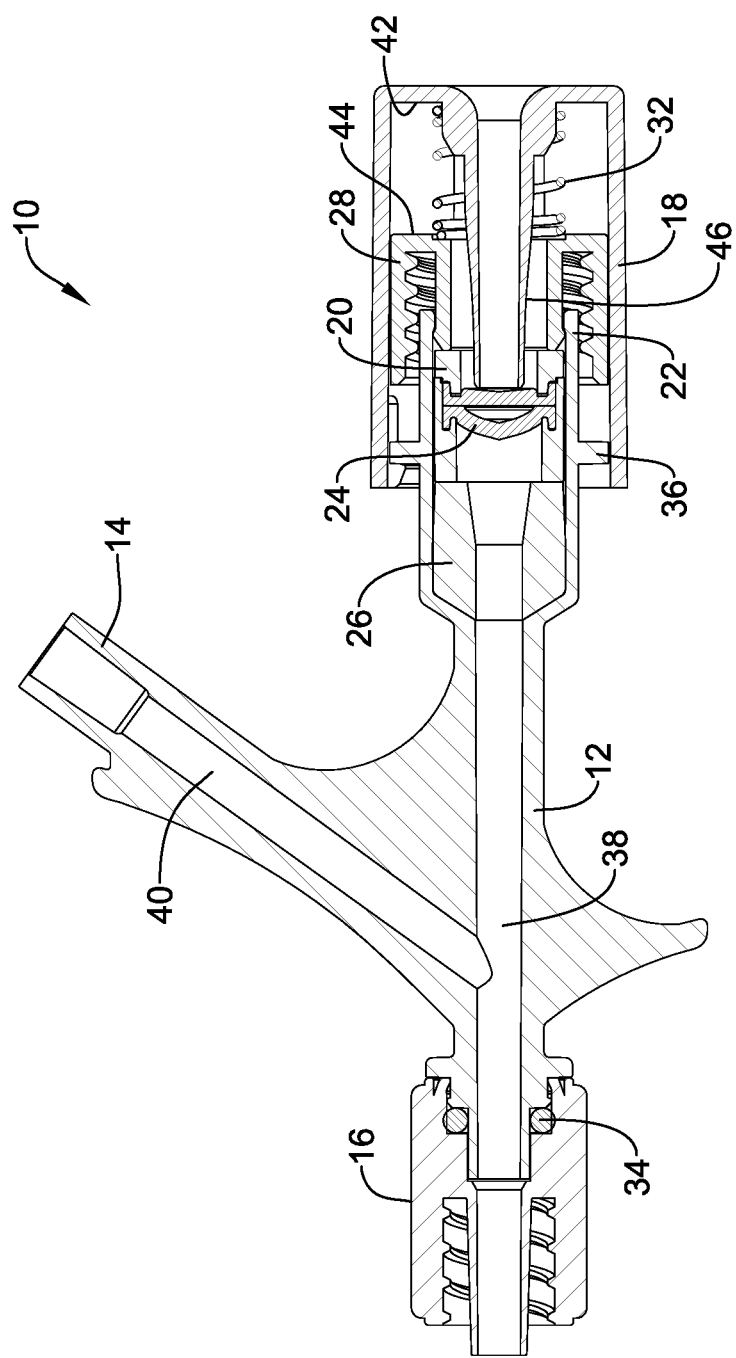
FIG. 3 is a cross-sectional view taken through line 3-3 in FIG. 1.

FIG. 3 is a cross-sectional view the hemostasis valve 10 along line 3-3 of FIG. 1. Here some of the structural features of the hemostasis valve 10 can be seen. For example, the hemostasis valve 10 may include a central lumen 38. In general, the central lumen 38 is designed to be placed into fluid communication with one or more lumens of a device coupled to the adapter 16. A second or infusion lumen 40 may be defined adjacent to the side port 14. The second lumen 40 may be in fluid communication with the central lumen 38.

As indicated above, the hemostasis valve 10 is designed so that it may be coupled to another device. For example, the adapter 16, which may take the form of a Tuohy-Borst or other type of connector, may be engaged with the proximal end of the other device. When connected (and with the plunger 18 in the configuration shown in FIG. 3), the second seal member 26 may be in an open state or configuration. Conversely, the first seal member 24 may be in a closed or sealed configuration when the hemostasis valve 10 is connected to the other device (and with the plunger 18 in the configuration shown in FIG. 3).

Collectively, when the hemostasis valve 10 is connected to another device and in the configuration shown in FIG. 3, the hemostasis valve 10 is able to substantially hold a fluid-tight seal that substantially prevents the backflow and/or leakage of body fluids (e.g., blood). At some point during a medical intervention, it may be desirable to infuse additional fluids such as contrast media through the hemostasis valve 10. This may include attaching an infusion device to the side port 14. Because the first seal member 24 may be designed to substantially prevent the backflow and/or leakage of relatively-low pressure fluids, if the infusion device infuses fluids at a relatively high pressure, it is possible that the infusion fluid may be able to flow through the first seal member 24.

Figure 4:
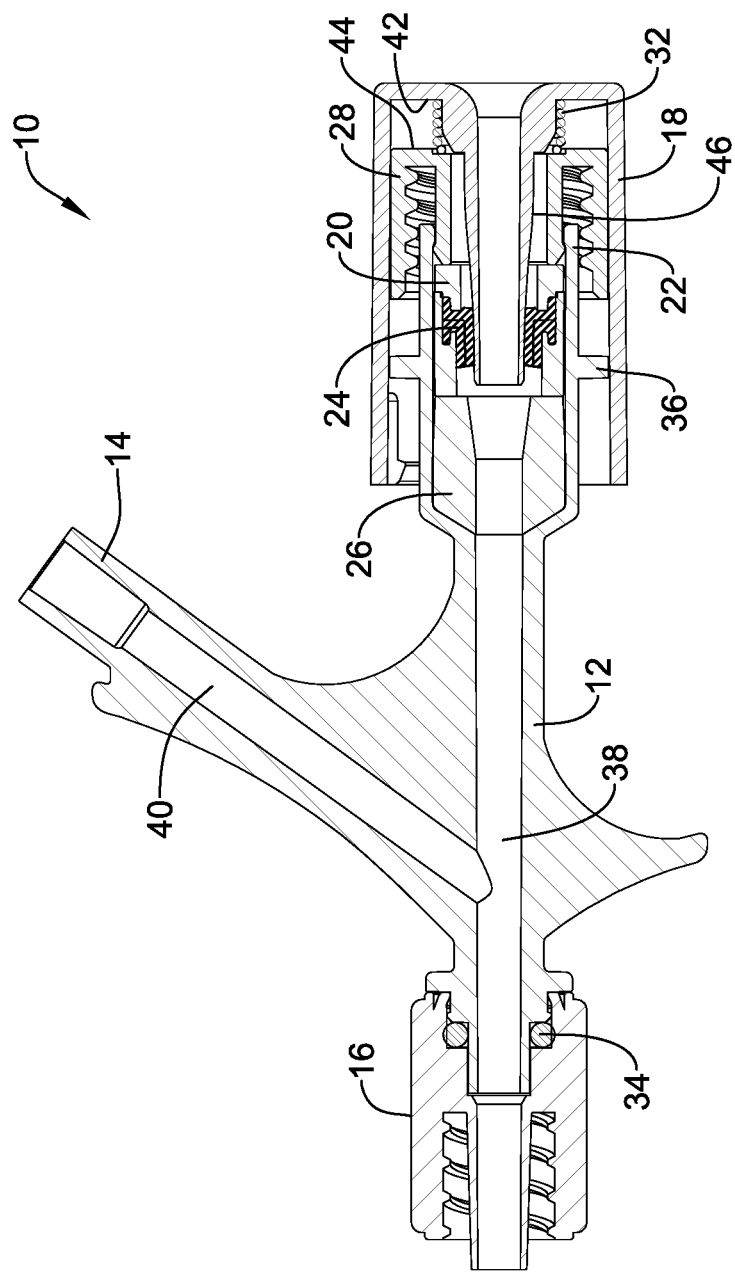
FIG. 4 is a cross-sectional view of an example hemostasis valve.
Figure 5:
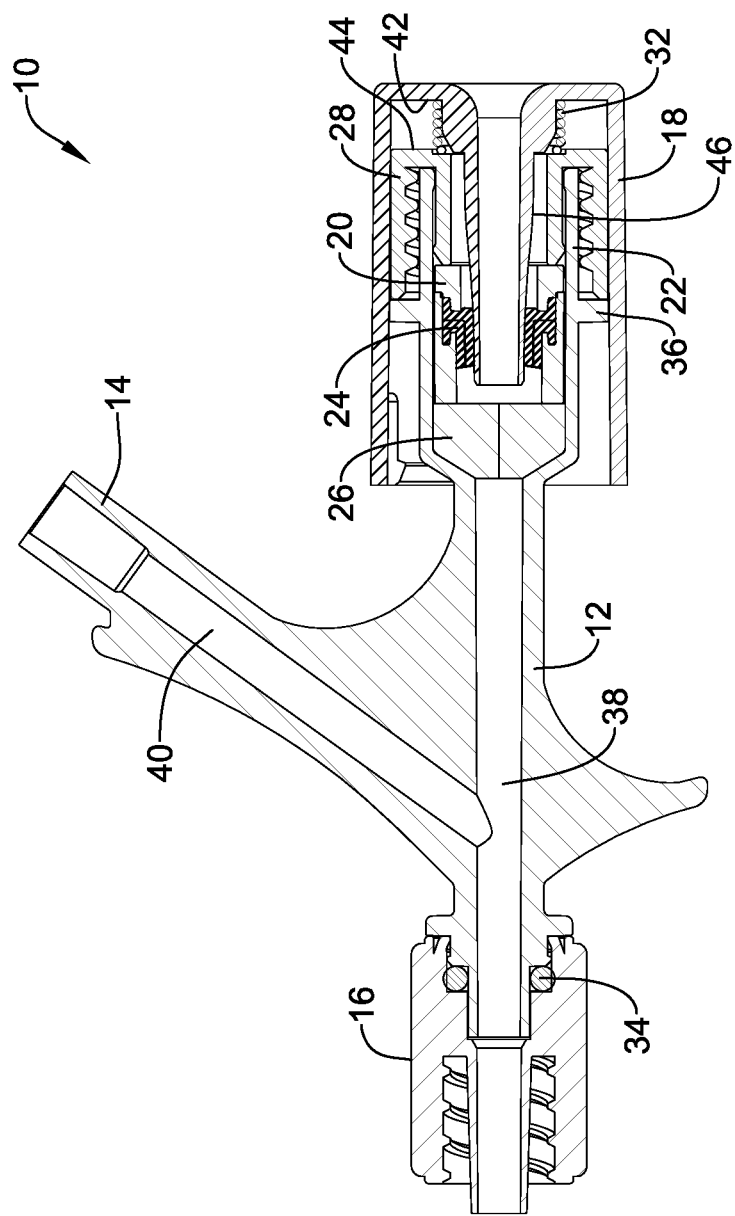
FIG. 5 is a cross-sectional view of an example hemostasis valve.
Figure 6:
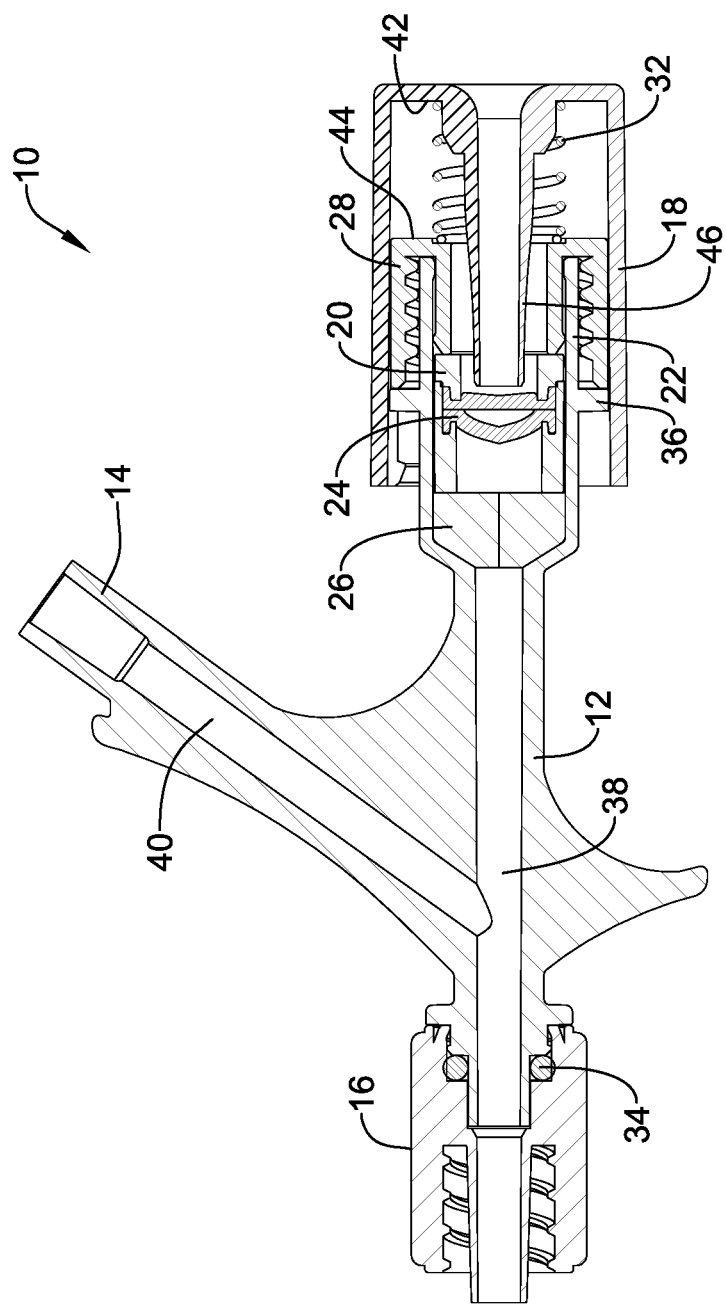
FIG. 6 is a cross-sectional view of an example hemostasis valve.

In order to prevent backflow of relatively high pressure fluids, the hemostasis valve 10 can be actuated to close or "seal" the second seal member 26. To do so, the plunger 18 may initially be urged distally until a distally-facing, proximal end surface or cap 42 of the plunger 18 is disposed adjacent to a proximal end region 44 of the nut 28, as shown in FIG. 4. When doing so, a tubular region 46 of the plunger 18 may extend through (and open) the first seal member 24. In addition, a portion of the plunger 18 may move distally beyond the ring member 36. With the cap 42 of the plunger 18 disposed adjacent to the nut 28, the plunger 18 can be rotated (e.g., in a clockwise direction) to close the second seal member 26, as shown in FIG. 5. This rotation may cause the nut 28 to rotate and move distally. Because the distal end region of the nut 28 may be engaged with the cartridge 20, distal movement of the nut 28 urges the cartridge 20 distally within the proximal end region 22 of the main body 12 such that the cartridge 20 engages and deforms the second seal member 26, thereby shifting the second seal member 26 to the closed or sealed configuration. The plunger 18 may be released or otherwise allowed to move proximally, as shown in FIG. 6, which may reclose the first seal member 24 (while the second seal member 26 remains closed). For example, the spring member 32 urge the plunger 18 toward the first position.

For the purposes of this disclosure, "clockwise" rotation of the plunger 18 and/or nut 28 may be understood as rotation of the plunger 18 in a clockwise direction relative to the main body 12 when looking at the plunger 18 from its proximal end. Similarly, "counter-clockwise" rotation of the plunger 18 and/or nut 28 may be understood as rotation of the plunger 18 in a counter-clockwise direction relative to the main body 12 when looking at the plunger 18 from its proximal end. This convention for clockwise/counter-clockwise is used throughout this disclosure.

In at least some instances, the first seal member 24 may be in a natively closed or sealed configuration. In other words, when not acted upon by other instruments, the first seal member 24 may be considered to be closed. In order to pass other medical devices through the hemostasis valve, it may be desirable to open the first seal member 24. To do so, the plunger 18 may be shifted from a first position (e.g., a proximal position as shown in FIG. 3) to a second position (e.g., a distal position as shown in FIG. 4). When doing so, the tubular region 46 of the plunger 18 may engage and ultimately pass through the first seal member 24 (e.g., as shown in FIG. 5). With the first seal member 24 opened, another medical device can more easily pass therethrough. Because the spring member 32 may be designed to urge the plunger 18 toward the first position (e.g., urge plunger 18 proximally), a user may need to maintain the plunger 18 in the second position manually.

In some instances, it may require the use of multiple hands (e.g., both hands of the user) in order to open (and maintain open) a seal within a hemostasis valve and advance another medical device through the seal. Disclosed herein are hemostasis valves that allow a user to both open a seal and advance another medical device therethrough with only one hand. Some additional details regarding these hemostasis devices are disclosed herein.

Figure 7:
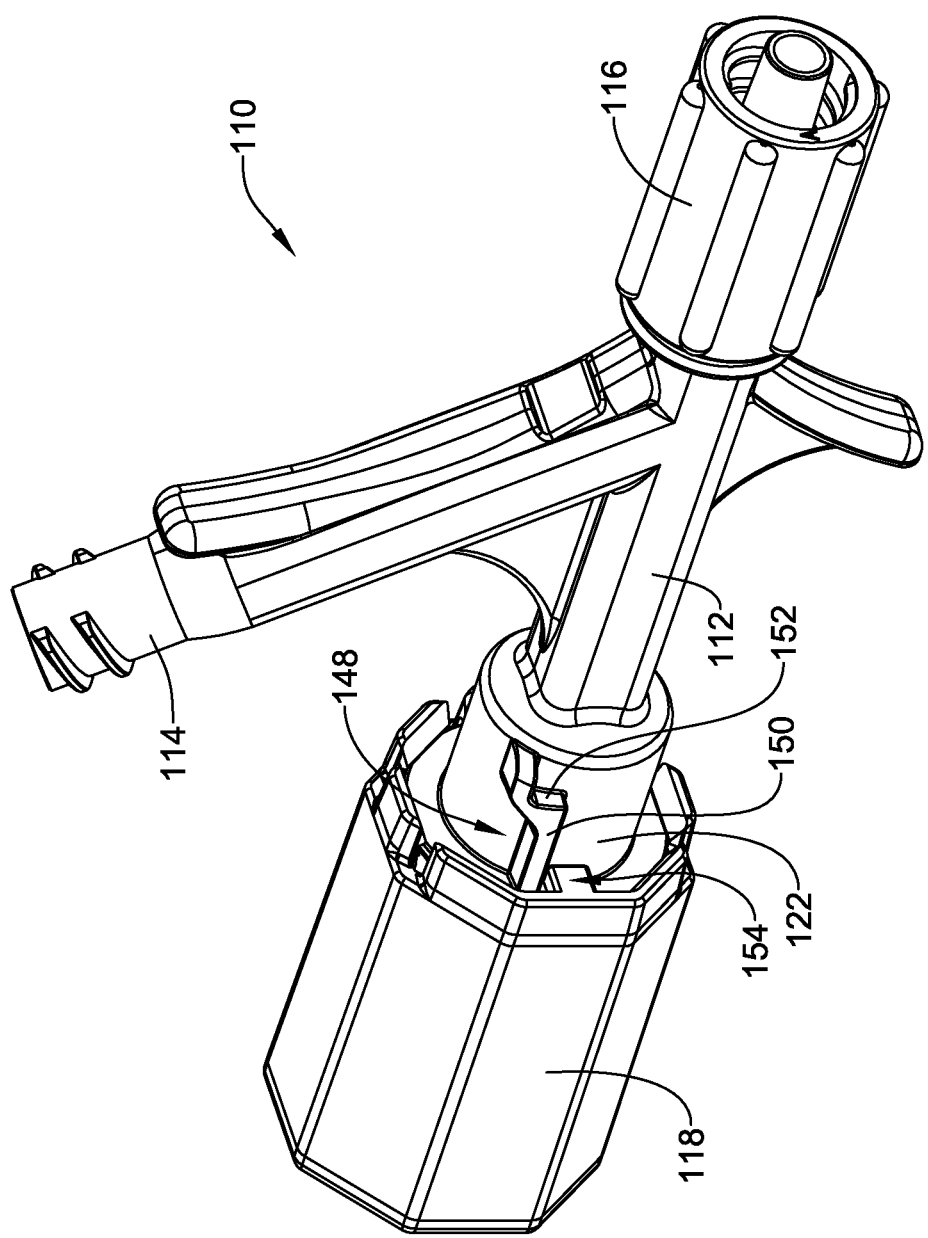
FIG. 7 is a perspective view of an example hemostasis valve.

FIG. 7 is a perspective view of another example hemostasis valve 110 that may be similar in form and function to other hemostasis valves disclosed herein. As such, the structural features of the hemostasis valve 110 can be utilized with any of the other hemostasis valves disclosed herein, to the extent applicable. The hemostasis valve 110 may include a main body 112, a side port 114, an adapter 116, a plunger 118, and a proximal end region 122. While not shown, the hemostasis valve 110 may include a first seal member (e.g., that may be similar in form and function to the first seal member 24 described herein and that may be disposed within a cartridge similar to the cartridge 20 described herein) and a second seal member (e.g., that may be similar in form and function to the second seal member 26 described herein).

A first locking member 148 may be disposed along the proximal end region 122 of the main body 112. The first locking member 148 may include a first projection region 150 disposed along the proximal end region 122 of the main body 112 that extends radially outward from the proximal end region 122 of the main body 112. A shoulder region 152 may be defined adjacent to and/or at the end of the first projection region 150. A second locking member 154 may be disposed along the plunger 118. The second locking member 154 may take the form of a second projection disposed along and radially inward from the plunger 118. A number of additional shapes and arrangements for the first locking member 148 and the second locking member 154 are contemplated.

Figure 8:
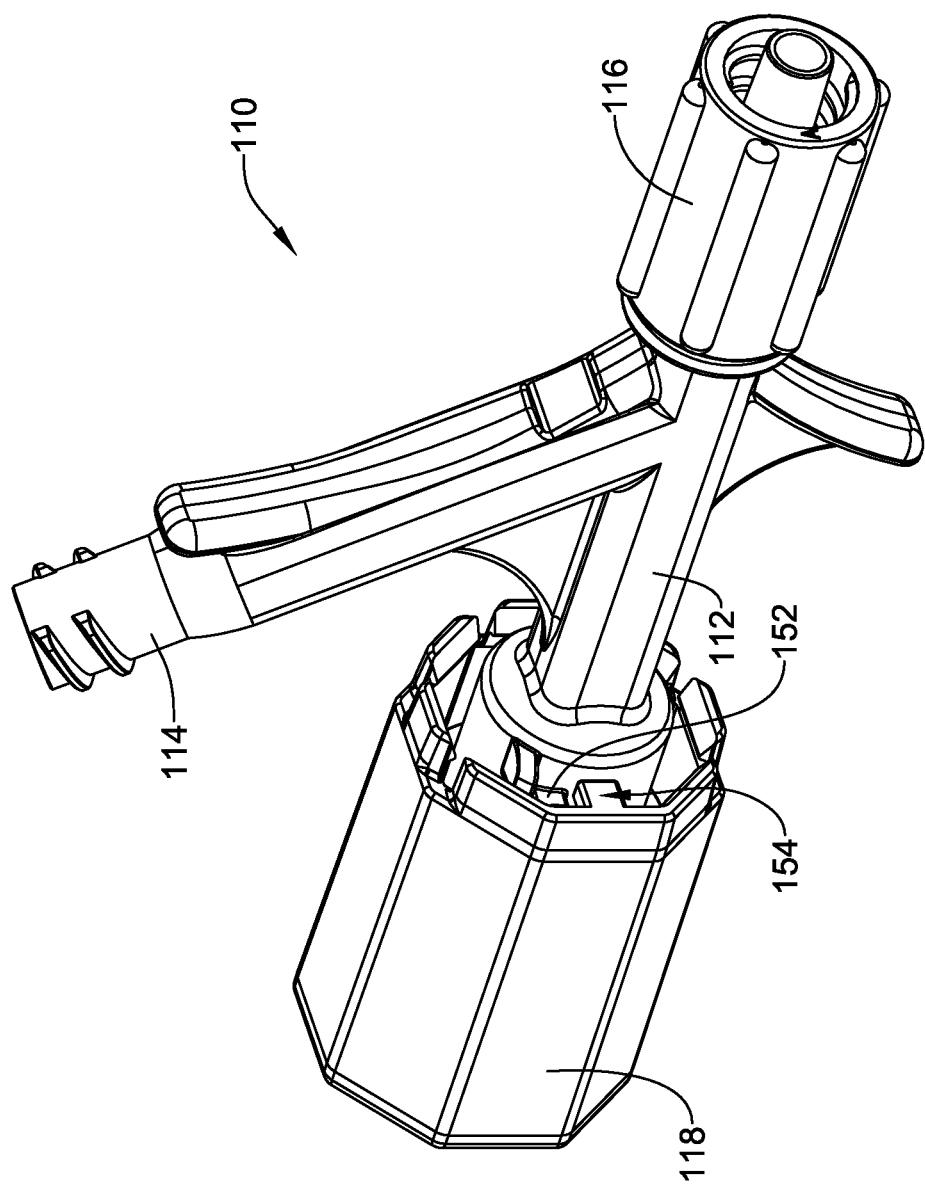
FIG. 8 is a perspective view of an example hemostasis valve.
Figure 9:
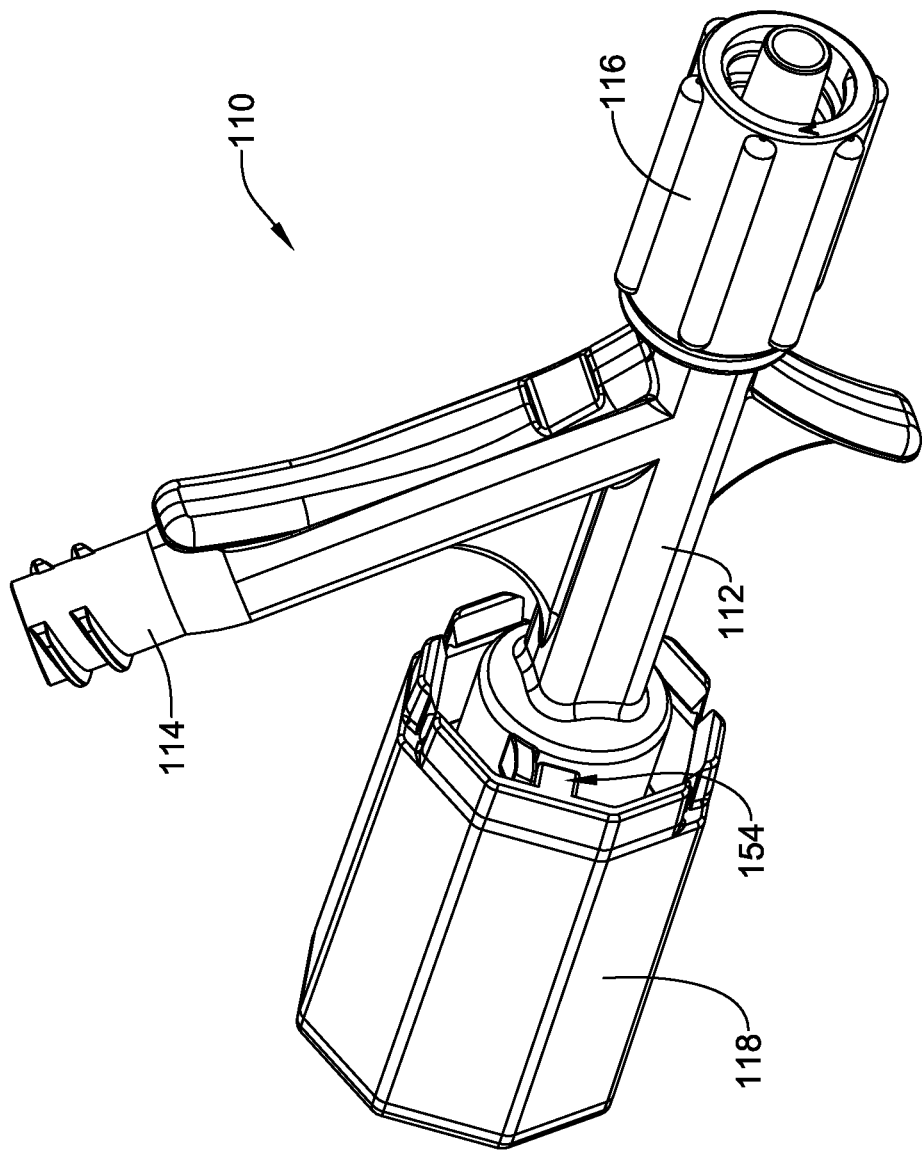
FIG. 9 is a perspective view of an example hemostasis valve.

When it is desired to open the first seal member so that another medical device may be extended through the hemostasis valve 110, the plunger may be shifted from a first position (e.g., as shown in FIG. 7) to a second position (e.g., as shown in FIG. 8), such that plunger 118 is urged distally in the second position relative to the first position. While at the second position, the plunger 118 may be rotated so that the second locking member 154 engages the first locking member 148, as shown in FIG. 9. When doing so, the second locking member 154 may engage the shoulder region 152 of the first locking member 148 such that the plunger 118 is maintained or otherwise held at the second position. Because engagement of the first locking member 148 with the second locking member 154 can occur by simply moving the plunger 118 distally (e.g., to the second position) and then rotating the plunger 118, a clinician can lock the plunger 118 at the second position using only one hand. Furthermore, the locking members 148/154 allow the first seal member to be maintained in an open configuration without having to apply additional force. In some instances, the rotation of the plunger 118 to engage the first locking member 148 with the second locking member 154 is in a first direction. The first direction may be counterclockwise. Rotation of the plunger 118 in a second direction (e.g., opposite the first direction) may result in the second seal member shifting to a closed/sealed configuration. The second direction may be clockwise.

Figure 10:
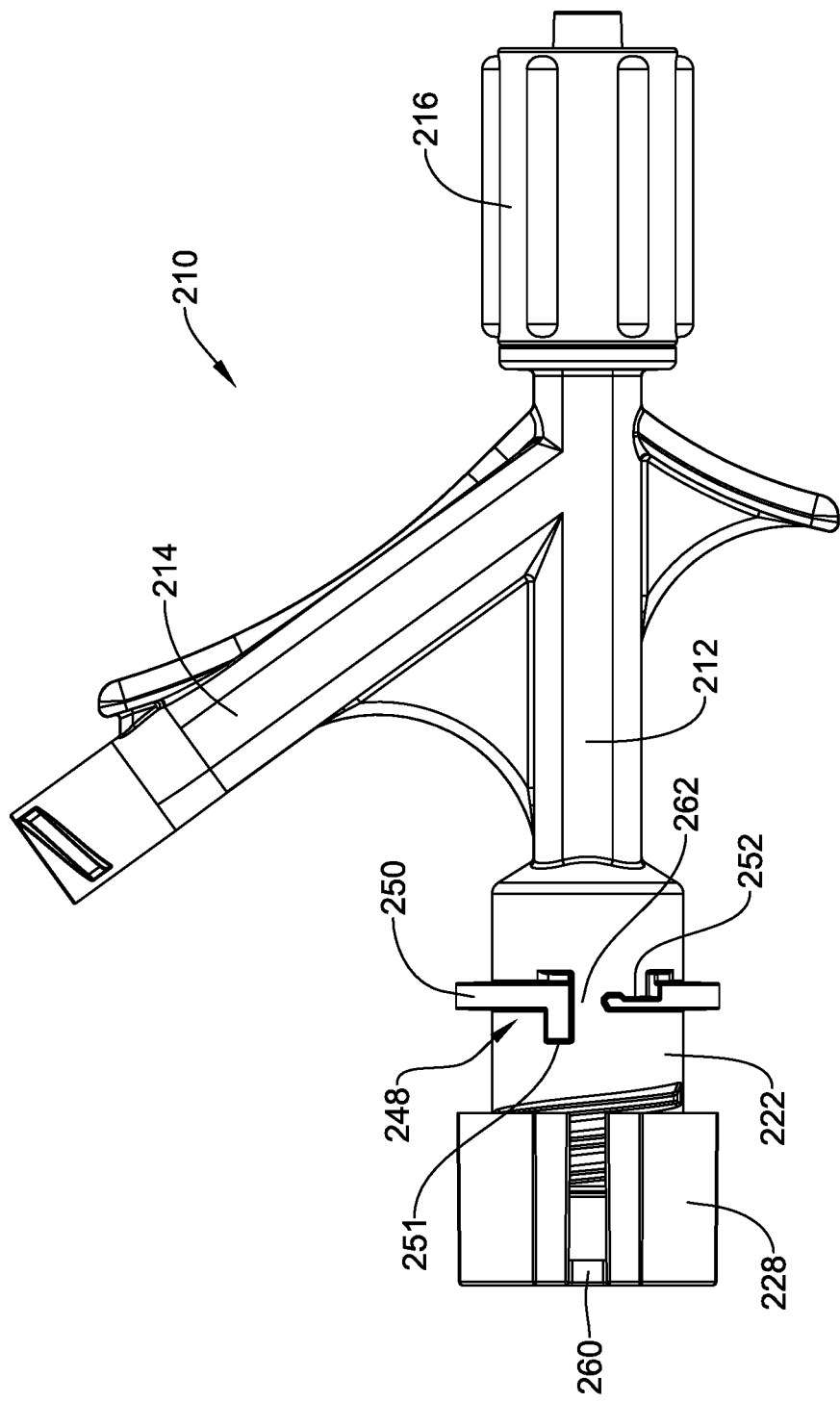
FIGS. 10-12 illustrate an example hemostasis valve.
Figure 11:
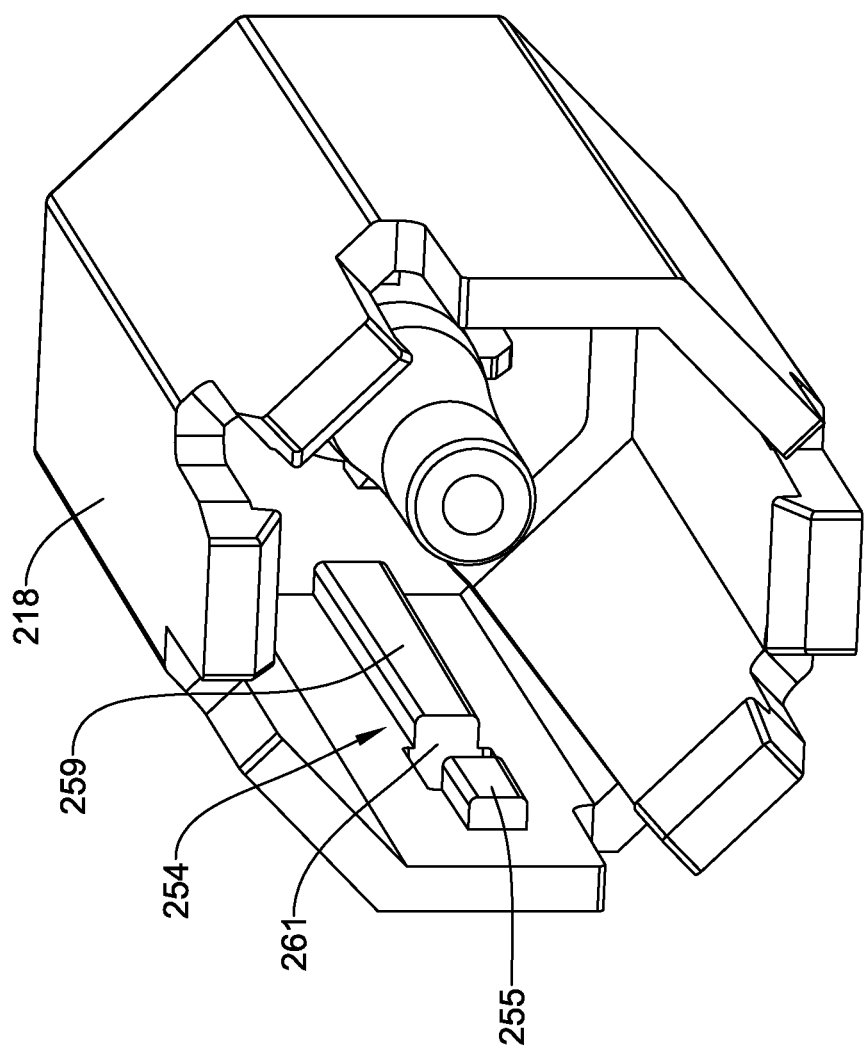
Figure 12:
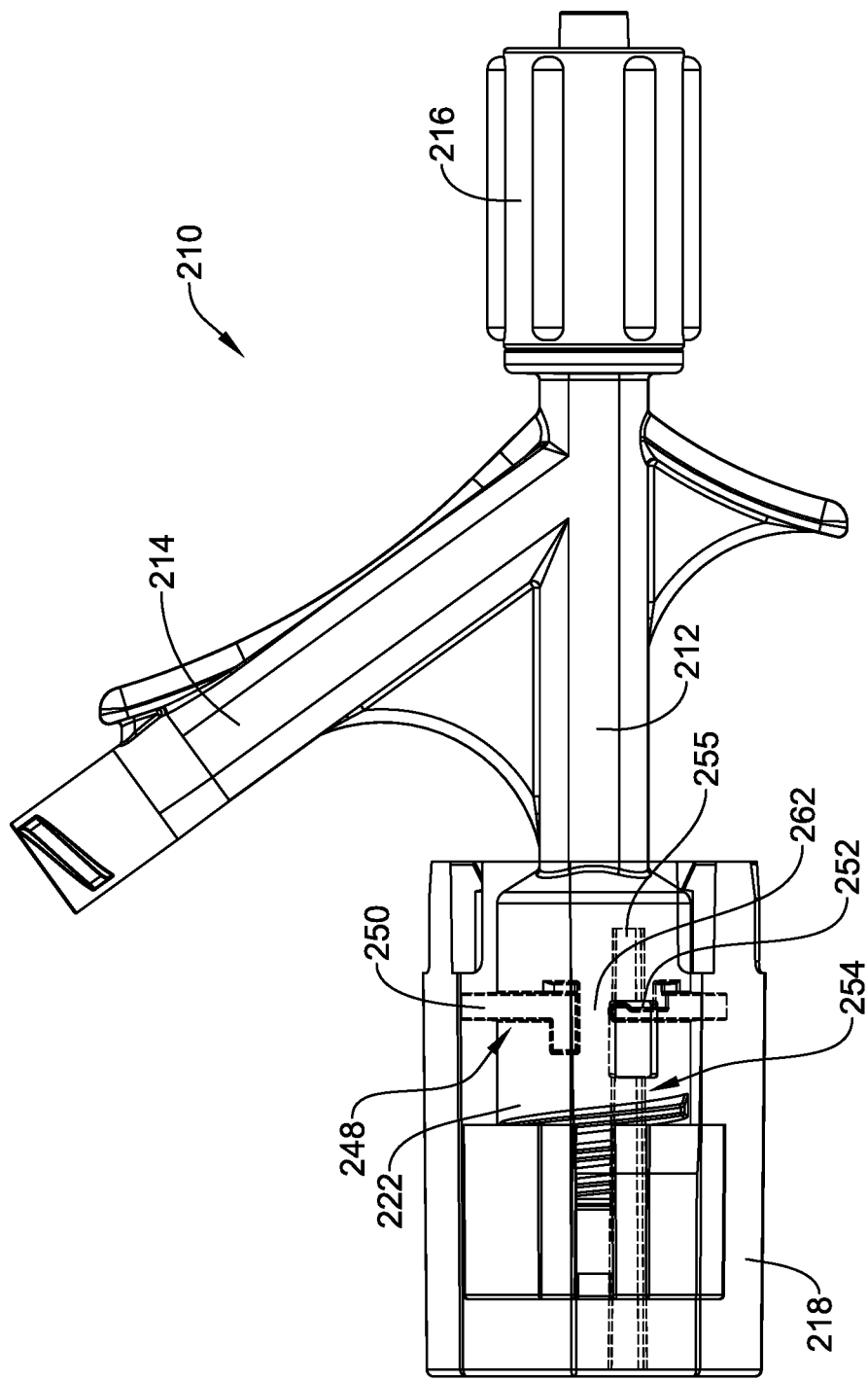

FIGS. 10-12 illustrate another example hemostasis valve 210 that may be similar in form and function to other hemostasis valves disclosed herein. As such, the structural features of the hemostasis valve 210 can be utilized with any of the other hemostasis valves disclosed herein, to the extent applicable. The hemostasis valve 210 may include a main body 212, a side port 214, an adapter 216, a plunger 218 (not shown in FIG. 10, can be seen in FIGS. 11-12), a nut 228 having an axial slot 260 formed therein, and a proximal end region 222 of the main body 212. While not shown, the hemostasis valve 210 may include a first seal member (e.g., that may be similar in form and function to the first seal member 24 described herein and that may be disposed within a cartridge similar to the cartridge 20 described herein) and a second seal member (e.g., that may be similar in form and function to the second seal member 26 described herein).

A first locking member 248 may be disposed along the proximal end region 222 of the main body 212. The first locking member 248 may include an annular region 250, a proximally-extending region 251, and a shoulder region 252. An opening 262 may be formed in the annular portion 250. As shown in FIGS. 11-12, a second locking member 254 may be disposed along the plunger 218. The second locking member 254 may include a distal portion 255, a proximal portion 259, and a slot 261 therebetween.

In use, much like the plunger 118, the plunger 218 may be shifted from a first (e.g., proximal) position to a second (e.g., distal) position. When the plunger 218 is at the second position, the plunger 218 may open the first seal member. The plunger 218 may be rotated so that the second locking member 254 engages the first locking member 248. For example, the second locking member 254 may be passed through the opening 262 and then rotated so that the distal portion 255 of the second locking member 254 engages or otherwise rests on the shoulder region 252 as depicted in FIG. 12. When doing so, the plunger 218 may be held at the second (e.g., distal) position with the first seal member open. In this example, locking the plunger 218 is accomplished by shifting the plunger to the second position and then rotating the plunger 218 is first direction (e.g., clockwise). Closing the second seal member may occur by further rotating the plunger 218 in the same (e.g., clockwise) direction.

Figure 13:
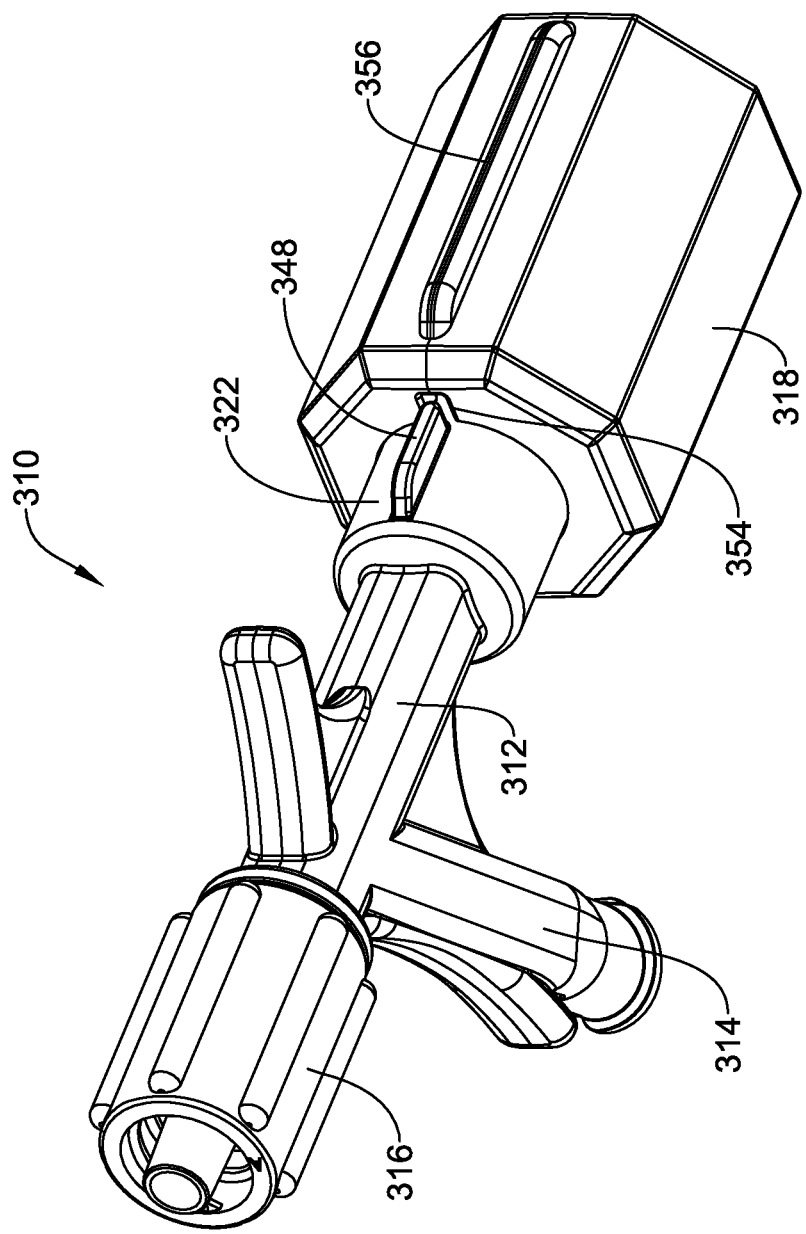
FIG. 13 is a perspective view of an example hemostasis valve.

FIG. 13 is a perspective view of another example hemostasis valve 310 that may be similar in form and function to other hemostasis valves disclosed herein. As such, the structural features of the hemostasis valve 310 can be utilized with any of the other hemostasis valves disclosed herein, to the extent applicable. The hemostasis valve 310 may include a main body 312, a side port 314, an adapter 316, a plunger 318, and a proximal end region 322. While not shown, the hemostasis valve 310 may include a first seal member (e.g., that may be similar in form and function to the first seal member 24 described herein and that may be disposed within a cartridge similar to the cartridge 20 described herein) and a second seal member (e.g., that may be similar in form and function to the second seal member 26 described herein).

Figure 14:
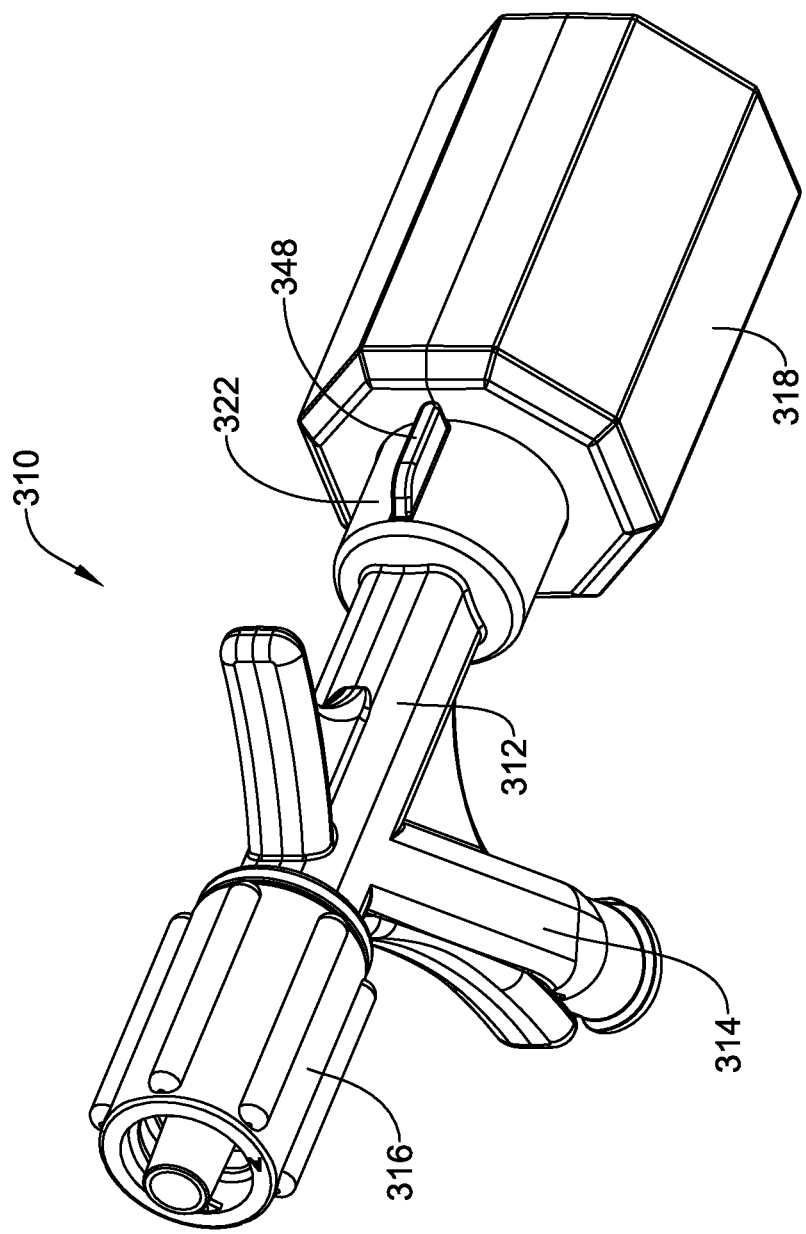
FIG. 14 is a perspective view of an example hemostasis valve.

The proximal end region 322 of the main body 312 may include a rib 348. A slot 354 may be disposed along the plunger 318. In some instances, an alignment member 356 may be disposed along the plunger 318. For example, the alignment member 356 may be disposed along an outer surface of the plunger 318. The rib 348, slot 354, and alignment member 356 may be utilized to assess whether or not the second seal member is in an open configuration or a closed configuration. For example, the rib 348 and the slot 354 may allow the plunger 318 to be moved distally (e.g., to a second position) when the rib 348 and the slot 354 are aligned. The alignment member 356 may be aligned with the slot 354. Once the plunger 318 is moved to the second position, the plunger 318 can be rotated to close the second seal member. The plunger 318 can then be allowed to move back to the first position, as depicted in FIG. 14, with the slot 354 and the alignment member 356 not aligned with the rib 348, so as to prevent distal movement of the plunger 318 (e.g., in FIG. 14, the alignment member 356 is rotated out of view). Because the alignment member 356 may be aligned with the slot 354, rotation of the plunger 318 may cause the alignment member 356 to rotate out of alignment with the rib 348. This provides a visual indicator to the user that the plunger 318 has been rotated and that the second seal member is closed/sealed.

Figure 15:
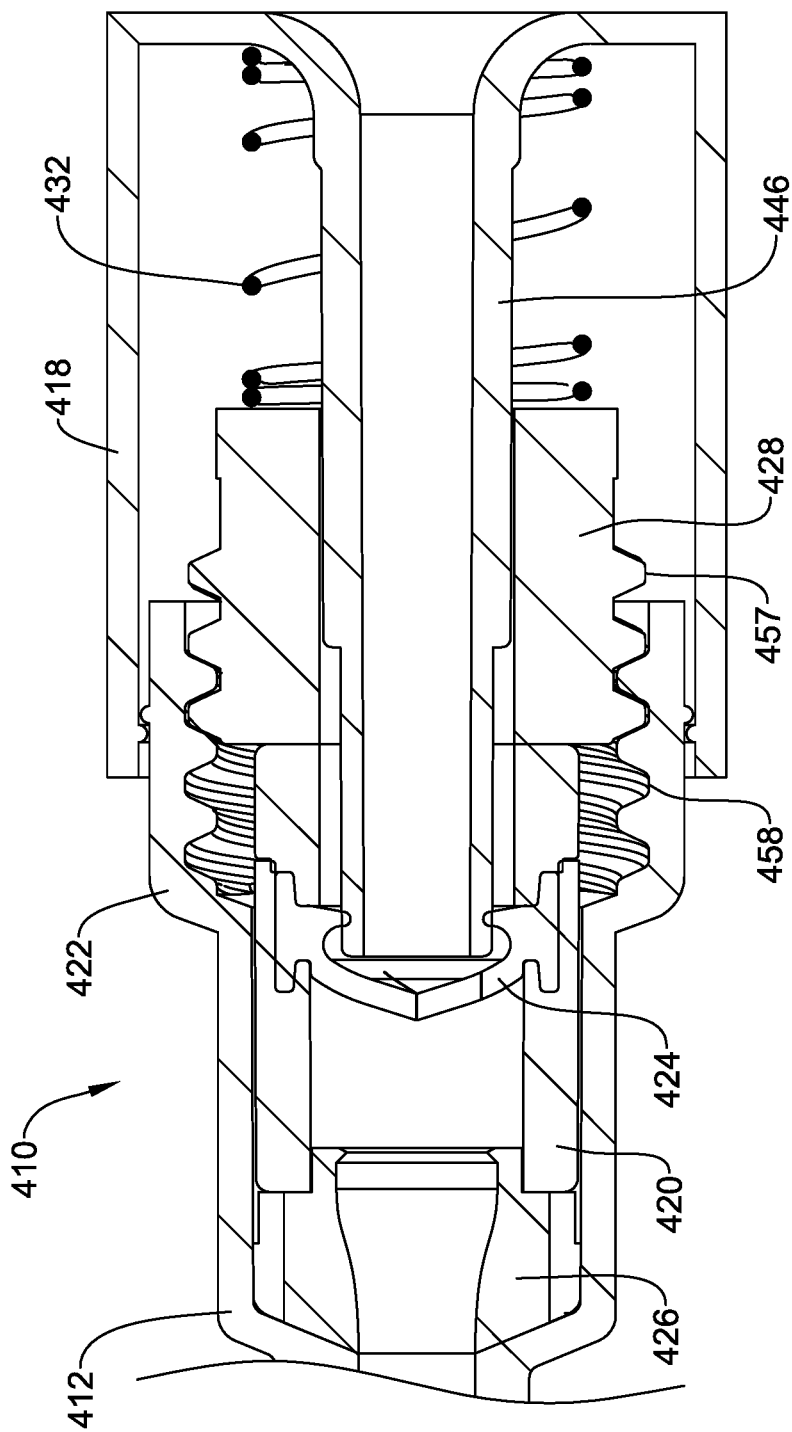
FIG. 15 is a partial cross-sectional view of a portion of an example hemostasis valve.

FIG. 15 is a partial cross-sectional view of a portion of another example hemostasis valve 410 that may be similar in form and function to other hemostasis valves disclosed herein. As such, the structural features of the hemostasis valve 410 can be utilized with any of the other hemostasis valves disclosed herein, to the extent applicable. The hemostasis valve 410 may include a main body 412, a plunger 418, a tubular region 446, a spring 432, and a proximal end region 422. A first seal member 424 may be disposed within the proximal end region 422 (e.g., within a cartridge 420). A second seal member 426 may also be disposed within the proximal end region 422.

A compression member 428 may be coupled to the proximal end region 422. In this example, the compression member 428 takes the form of a nut with an external thread 457. The external thread 457 may be designed to threadably engage with an internal thread 458 disposed along the proximal end region 422. The use of the internal thread 458 along the proximal end region 422 of the main body 412 and an "internal" nut 428 having the external thread 457 may allow the profile of the hemostasis valve 410 to be reduced.

The materials that can be used for the various components of the hemostasis valve 10 (and/or other hemostasis valves disclosed herein) and the various components thereof disclosed herein may include those commonly associated with medical devices. For simplicity purposes, the following discussion makes reference to the main body 12 and other components of the hemostasis valve 10. However, this is not intended to limit the devices and methods described herein, as the discussion may be applied to other hemostasis valves and/or components thereof disclosed herein.

The main body 12 and/or other components of the hemostasis valve 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:
1. A hemostasis valve, comprising:
 a main body having a distal end region and a proximal end region;
 a first seal member disposed within the proximal end region of the main body;
 a second seal member disposed at least partially within the main body;
 a compression member coupled to the proximal end region of the main body, the compression member being designed to shift the second seal member between an open configuration and a sealed configuration;
 a plunger coupled to the proximal end region of the main body, the plunger being designed to shift between a first position and a second position;
 a first locking member disposed along the proximal end region of the main body;
 a second locking member disposed along the plunger, the second locking member being designed to engage the first locking member; and
 wherein the plunger is designed to rotate the compression member and shift the second seal member to the sealed configuration when the plunger is rotated in a first direction while the plunger is at the second position, and wherein the plunger is designed to engage the first locking member with the second locking member and maintain the plunger in the second position when the plunger is rotated in a second direction different from the first direction while the plunger is at the second position.

2. The hemostasis valve of claim 1, further comprising a cartridge at least partially disposed within the proximal end region of the main body, wherein the first seal is within the cartridge.

3. The hemostasis valve of claim 1, wherein the first seal member is designed to be in a natively closed configuration.

4. The hemostasis valve of claim 3, wherein the plunger is designed to open the first seal member when shifted to the second position.

5. The hemostasis valve of claim 1, wherein the plunger is designed to engage the first locking member with the second locking member and maintain the plunger in the second position.

6. The hemostasis valve of claim 1, wherein the first locking member includes a first projection region disposed along the proximal end region of the main body and extending radially outward from the proximal end region of the main body.

7. The hemostasis valve of claim 6, wherein a shoulder region is defined adjacent to the first projection region.

8. The hemostasis valve of claim 1, wherein the first locking member includes an annular region having an opening formed therein.

9. The hemostasis valve of claim 1, wherein the second locking member includes a second projection region disposed along the plunger extending radially inward from the plunger.

10. The hemostasis valve of claim 1, further comprising:
a rib disposed along the proximal end region of the main body;
a slot disposed along the plunger, the slot configured to receive the rib; and
an alignment member disposed along an outer surface of the plunger, the alignment member corresponding to a position of the slot.

11. The hemostasis valve of claim 1, wherein the compression member includes a nut threadably engaged with an external thread disposed along an outer surface of the proximal end region of the main body.

12. The hemostasis valve of claim 1, wherein the compression member includes a nut threadably engaged with an internal thread disposed along an inner surface of the proximal end region of the main body.

13. A hemostasis valve, comprising:
a main body having a distal end region and a proximal end region;
a cartridge at least partially disposed within the proximal end region of the main body, the cartridge including a first seal member;
wherein the first seal member is designed to be in a natively closed configuration;
a second seal member disposed within the proximal end region of the main body;
a nut coupled to the proximal end region of the main body, the nut being designed to shift the second seal member between an open configuration and a sealed configuration;
a plunger coupled to the proximal end region of the main body, the plunger being designed to shift between a first axial position and a second axial position;
wherein shifting the plunger to the second axial position opens the first seal member;
a first locking member disposed along the proximal end region of the main body;
a second locking member disposed along the plunger;
wherein rotating the plunger in a first direction while the plunger is at the second axial position rotates the nut and shifts the second seal member from the open configuration to the sealed configuration; and
wherein rotating the plunger in a second direction while the plunger is at the second axial position engages the first locking member with the second locking member and maintains the plunger at the second axial position.

14. The hemostasis valve of claim 13, wherein the nut is threadably engaged with an external thread disposed along an outer surface of the proximal end region of the main body.

15. The hemostasis valve of claim 13, wherein the nut is threadably engaged with an internal thread disposed along an inner surface of the proximal end region of the main body.

16. The hemostasis valve of claim 13, wherein the first locking member includes a first projection disposed along the proximal end region of the main body and extending radially outward from the proximal end region of the main body, wherein a shoulder region is defined along the first projection.

17. A method for using a hemostasis valve, the method comprising:
securing a hemostasis valve to a medical device, the hemostasis valve comprising:
a main body having a distal end region and a proximal end region;
a first seal member disposed within the proximal end region of the main body,
wherein the first seal member is designed to be in a natively closed configuration,
a second seal member disposed at least partially within the main body,
a compression member coupled to the proximal end region of the main body, the compression member being designed to shift the second seal member between an open configuration and a sealed configuration,
a plunger coupled to the proximal end region of the main body, the plunger being designed to shift between a first axial position and a second axial position,
a first locking member disposed along the proximal end region of the main body, and
a second locking member disposed along the plunger;
shifting the plunger to the second axial position to open the first seal member; and
rotating the plunger in a first direction while the plunger is at the second axial position to engage the first locking member with the second locking member and maintain the plunger at the second axial position, and
further rotating the plunger in the first direction to rotate the compression member and shift the second seal member to the sealed configuration.

18. The method of claim 17, further comprising rotating the plunger in a second direction opposite the first direction while the plunger is at the second axial position.

* * * * *